US009072900B2

(12) United States Patent
Caspi et al.

(10) Patent No.: US 9,072,900 B2
(45) Date of Patent: *Jul. 7, 2015

(54) SPATIAL MAPPING FOR A VISUAL PROSTHESIS

(75) Inventors: Avraham Caspi, La Jolla, CA (US); Jessy Dorn, Los Angeles, CA (US); Matthew J. McMahon, Los Angeles, CA (US); Robert J. Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 999 days.

This patent is subject to a terminal disclaimer.

(21) Appl. No.: 13/094,210

(22) Filed: Apr. 26, 2011

(65) Prior Publication Data
US 2011/0202110 A1 Aug. 18, 2011

Related U.S. Application Data

(62) Division of application No. 12/114,657, filed on May 2, 2008, now Pat. No. 7,957,811.

(60) Provisional application No. 60/928,407, filed on May 8, 2007, provisional application No. 60/928,440, filed on May 8, 2007.

(51) Int. Cl.
*A61N 1/36* (2006.01)
(52) U.S. Cl.
CPC .......... *A61N 1/36046* (2013.01); *A61N 1/3605* (2013.01)

(58) Field of Classification Search
None
See application file for complete search history.

(56) References Cited

U.S. PATENT DOCUMENTS

| 5,109,844 | A | 5/1992 | de Juan, Jr. et al. | |
| 5,740,285 | A | 4/1998 | Bloomberg et al. | |
| 5,935,155 | A | 8/1999 | Humayun et al. | |
| 6,400,989 | B1 | 6/2002 | Eckmiller | |
| 6,458,157 | B1 | 10/2002 | Suaning | |
| 7,957,811 | B2* | 6/2011 | Caspi et al. | 607/54 |
| 2005/0182456 | A1* | 8/2005 | Ziobro et al. | 607/48 |
| 2006/0178711 | A1* | 8/2006 | Patrick et al. | 607/57 |
| 2007/0073358 | A1* | 3/2007 | Greenberg et al. | 607/54 |

FOREIGN PATENT DOCUMENTS

| WO | WO 01/91852 A1 | 12/2001 |
| WO | WO 02/089912 A2 | 11/2002 |
| WO | WO 2007/127444 A2 | 11/2007 |

* cited by examiner

*Primary Examiner* — Kennedy Schaetzle
(74) *Attorney, Agent, or Firm* — Scott B. Dunbar

(57) ABSTRACT

A visual prosthesis and a method of operating a visual prosthesis are disclosed. Neural stimulation through electrodes is controlled by spatial maps, where a grouped or random association is established between the data points of the acquired data and the electrodes. In this way distortions from the foveal pit and wiring mistakes in the implant can be corrected. Moreover, broken electrodes can be bypassed and a resolution limit can be tested, together with testing the benefit the patient receives from correct spatial mapping.

9 Claims, 6 Drawing Sheets

The present disclosure relates to operation of visual prostheses implants. More in particular, it relates to a spatial mapping for a visual prosthesis.

SPATIAL MAPPING FOR A VISUAL PROSTHESIS

CROSS REFERENCE TO RELATED APPLICATIONS

This application is a divisional application of U.S. patent applications Ser. No. 12/114,657, filed May 2, 2008 now U.S. Pat. No. 7,957,811, for "Spatial Mapping for a Visual Prosthesis" which claims priority to U.S. Provisional Application 60/928,407 filed on May 8, 2007 and U.S. Provisional Application 60/928,440 filed on May 8, 2007, the contents of both of which are incorporated herein by reference in their entirety. This application may also be related to U.S. application Ser. No. 12/114,557, filed May 2, 2008, for "Method And System For Providing Stimulation Inputs To A Visual Prosthesis Implant" the contents of which are also incorporated by reference in their entirety.

STATEMENT OF GOVERNMENT INTEREST

This invention was made with government support under grant No. R24EY12893-01, awarded by the National Institutes of Health. The government has certain rights in the invention.

FIELD

The present disclosure relates to operation of visual prostheses implants. More in particular, it relates to a spatial mapping for a visual prosthesis.

SUMMARY

According to a first aspect, a method of mapping relationship of pixels of an acquired image to electrodes of a visual prosthesis implant adapted to be positioned on the retina of a subject is provided, the method comprising: associating a plurality of pixels of the acquired image to form a group of pixels; associating a plurality of electrodes to form a group of electrodes; and mapping the group of pixels to the group of electrodes.

According to a second aspect, a visual prosthesis is provided, comprising: an implanted portion having a radiofrequency receiver and an array of electrodes suitable for stimulating visual neurons; and an external portion having a video processing unit and including a spatial redirection map, wherein the spatial redirection map establishes a relationship between an image acquired by the visual prosthesis and the array of electrodes, the relationship providing an association between an average pixel value of a plurality of pixels and a subset of the array of electrodes.

According to a third aspect, a method of mapping relationship of pixels of an acquired image to electrodes of a visual prosthesis implant adapted to be positioned on the retina of a subject is provided, the method comprising: dividing the acquired image in a plurality of areas, positioning the electrodes on the retina in a way that a one-to-one spatial relationship between each area and each electrode is implicitly established; and mapping each area to each pixel in a random one-to-one spatial relationship different from the implicitly established one-to-one spatial relationship.

According to a fourth aspect, a visual prosthesis is provided, comprising: an implanted portion having a radiofrequency receiver and an array of electrodes suitable for stimulating visual neurons; and an external portion having a video processing unit and including a spatial redirection map, wherein the spatial redirection map establishes a relationship between an image acquired by the visual prosthesis and the array of electrodes, the relationship providing a random association between each pixel value and each electrode of the array of electrodes.

Further embodiments of the present disclosure can be found in the written specification, drawings and claims of the present application.

Therefore, the present disclosure provides a flexible and arbitrary mapping between the input video image and the stimulation electrodes to correct distortions from the foveal pit, correct wiring mistakes in the implant, bypass broken electrodes using current summation to enable non-sensitive electrodes, test the resolution limit of the implant, test the benefit the patient receives from correct spatial mapping, and to solve orientation problems of the array on the retina.

DETAILED DESCRIPTION

Figure 1:
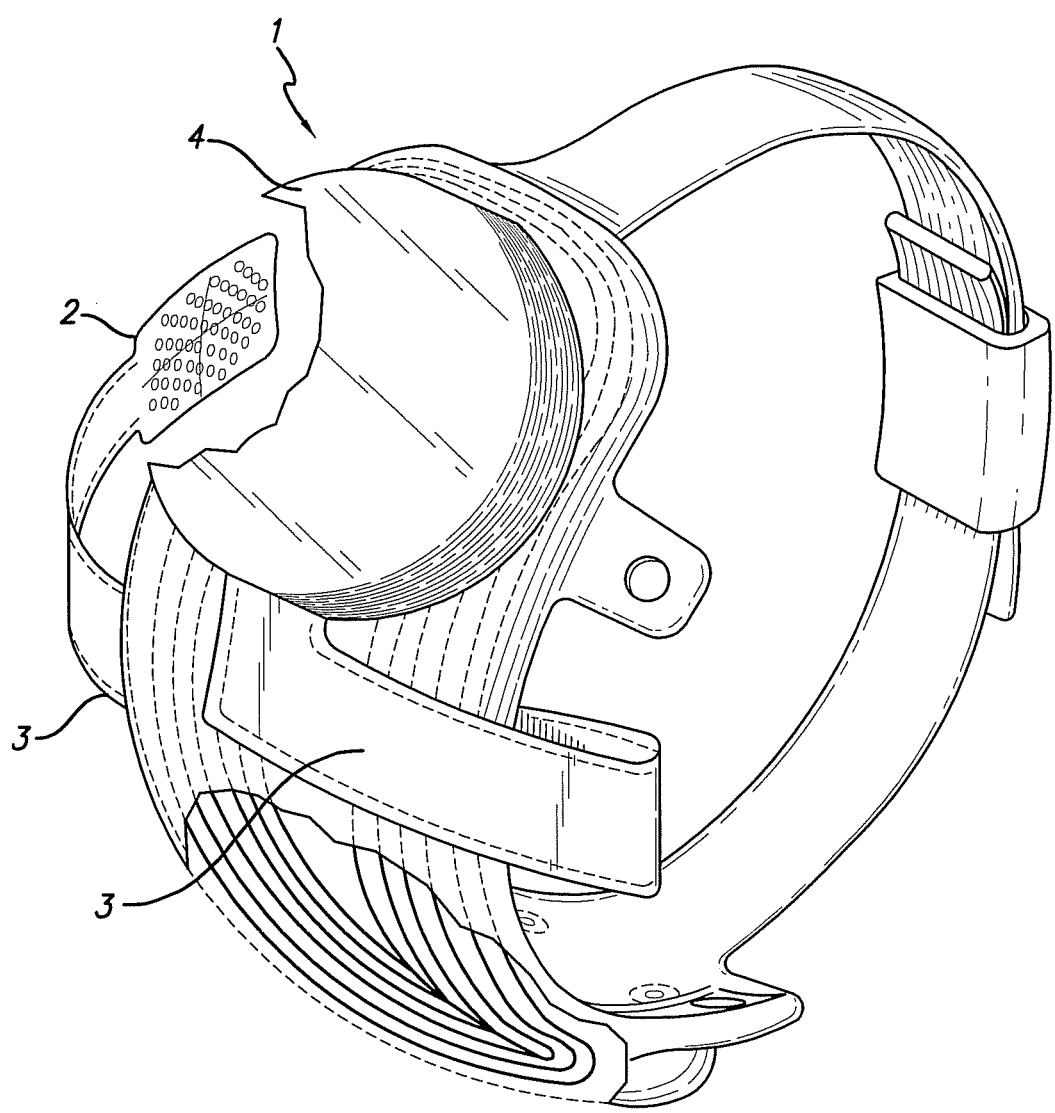
FIGS. 1 and 2 show a retinal stimulation system
Figure 2:
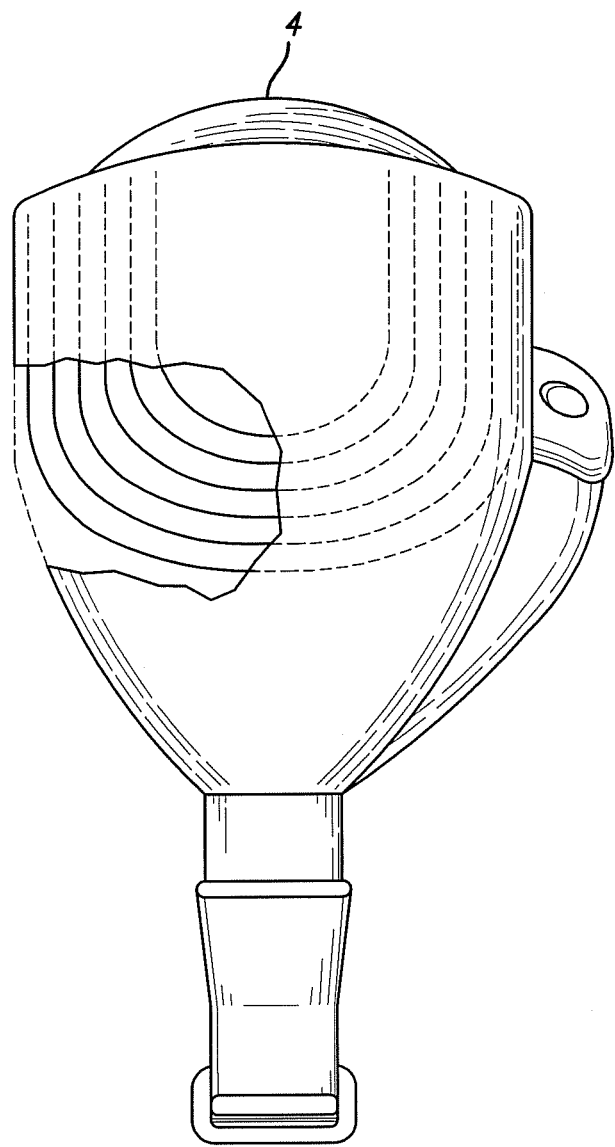

A Retinal Stimulation System, disclosed in U.S. application Ser. No. 11/207,644, filed Aug. 19, 2005 for "Flexible Circuit Electrode Array" by Robert J. Greenberg, et, al. incorporated herein by reference, is intended for use in subjects with retinitis pigmentosa. FIG. 1 and FIG. 2 show a Retinal Stimulation System (1) wherein a patient/subject is implanted with a visual prosthesis. Reference can also be made to FIGS. 1-5 of U.S. application Ser. No. 11/796,425, filed Apr. 27, 2007 for "Visual Prosthesis Fitting", also incorporated herein by reference in its entirety.

The Retinal Stimulation System (1) is an implantable electronic device containing electrode array (2) that is electrically coupled by a cable (3) that pierces sclera of the subject's eye and is electrically coupled to an electronics package (4), external to the sclera. The Retinal Stimulation System (1) is designed to elicit visual percepts in blind subjects with retinitis pigmentosa.

Figure 3:
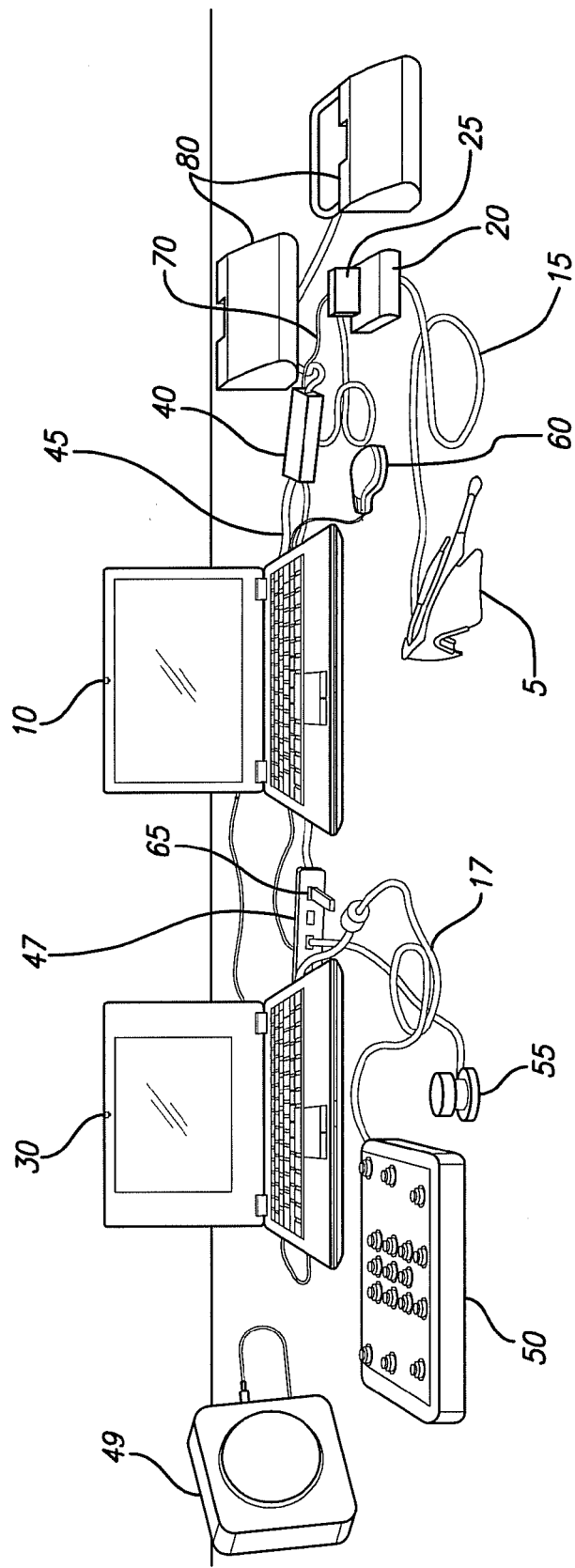
FIG. 3 shows components of a fitting system.

Referring to FIG. 3, a Fitting System (FS) may be used to configure and optimize the visual prosthesis (3) of the Retinal Stimulation System (1).

The Fitting System may comprise custom software with a graphical user interface (GUI) running on a dedicated laptop computer (10). Within the Fitting System are modules for performing diagnostic checks of the implant, loading and executing video configuration files, viewing electrode voltage waveforms, and aiding in conducting psychophysical experiments. A video module can be used to download a video configuration file to a Video Processing Unit (VPU) (20) and store it in non-volatile memory to control various aspects of video configuration, e.g. the spatial relationship between the video input and the electrodes, which is one of the main aspects of the present disclosure. The software can also load a previously used video configuration file from the VPU (20) for adjustment.

The Fitting System can be connected to the Psychophysical Test System (PTS), located for example on a dedicated laptop (30), in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB (MathWorks) software and other tools to allow the clinicians to develop customized psychophysics experiment scripts.

Any time stimulation is sent to the VPU (20), the stimulation parameters are checked to ensure that maximum charge per phase limits, charge balance, and power limitations are met before the test stimuli are sent to the VPU (20) to make certain that stimulation is safe.

Using the psychophysics module, important perceptual parameters such as perceptual threshold, maximum comfort level, and spatial location of percepts may be reliably measured.

Based on these perceptual parameters, the fitting software enables custom configuration of the transformation between video image and spatio-temporal electrode stimulation parameters in an effort to optimize the effectiveness of the retinal prosthesis for each subject.

The Fitting System laptop (10) is connected to the VPU (20) using an optically isolated serial connection adapter (40). Because it is optically isolated, the serial connection adapter (40) assures that no electric leakage current can flow from the Fitting System laptop (10).

As shown in FIG. 3, the following components may be used with the Fitting System according to the present disclosure. A Video Processing Unit (VPU) (20) for the subject being tested, a Charged Battery (25) for VPU (20), Glasses (5), a Fitting System (FS) Laptop (10), a Psychophysical Test System (PTS) Laptop (30), a PTS CD (not shown), a Communication Adapter (CA) (40), a USB Drive (Security) (not shown), a USB Drive (Transfer) (not shown), a USB Drive (Video Settings) (not shown), a Patient Input Device (RF Tablet) (50), a further Patient Input Device (Jog Dial) (55), Glasses Cable (15), CA-VPU Cable (70), CFS-CA Cable (45), CFS-PTS Cable (46), Four (4) Port USB Hub (47), Mouse (60), LED Test Array (80), Archival USB Drive (49), an Isolation Transformer (not shown), adapter cables (not shown), and an External Monitor (not shown).

The external components of a Fitting System may be configured as follows. The battery (25) is connected with the VPU (20). The PTS Laptop (30) is connected to FS Laptop (10) using the CFS-PTS Cable (46). The PTS Laptop (30) and FS Laptop (10) are plugged into the Isolation Transformer (not shown) using the Adapter Cables (not shown). The Isolation Transformer is plugged into the wall outlet. The four (4) Port USB Hub (47) is connected to the FS laptop (10) at the USB port. The mouse (60) and the two Patient Input Devices (50) and (55) are connected to four (4) Port USB Hubs (47). The FS laptop (10) is connected to the Communication Adapter (CA) (40) using the CFS-CA Cable (45). The CA (40) is connected to the VPU (20) using the CA-VPU Cable (70). The Glasses (5) are connected to the VPU (20) using the Glasses Cable (15).

In a visual prosthesis, every electrode in the implanted array of electrodes produces a spot of light (phosphene) in the visual field. A transformation needs to be specified to map the stimulation of individual electrodes in the stimulating array to specific locations, or regions, in the acquired video image. This transformation is specified in a look-up table referred to as the spatial map. In other words, spatial mapping is the relationship of a pixel, or pixels, in the camera's view to an electrode on the retina. Due to the optics of the eye, the retina is laid out reverse of the real world and proportional. The scale depends on the distance of the object.

Figure 4:
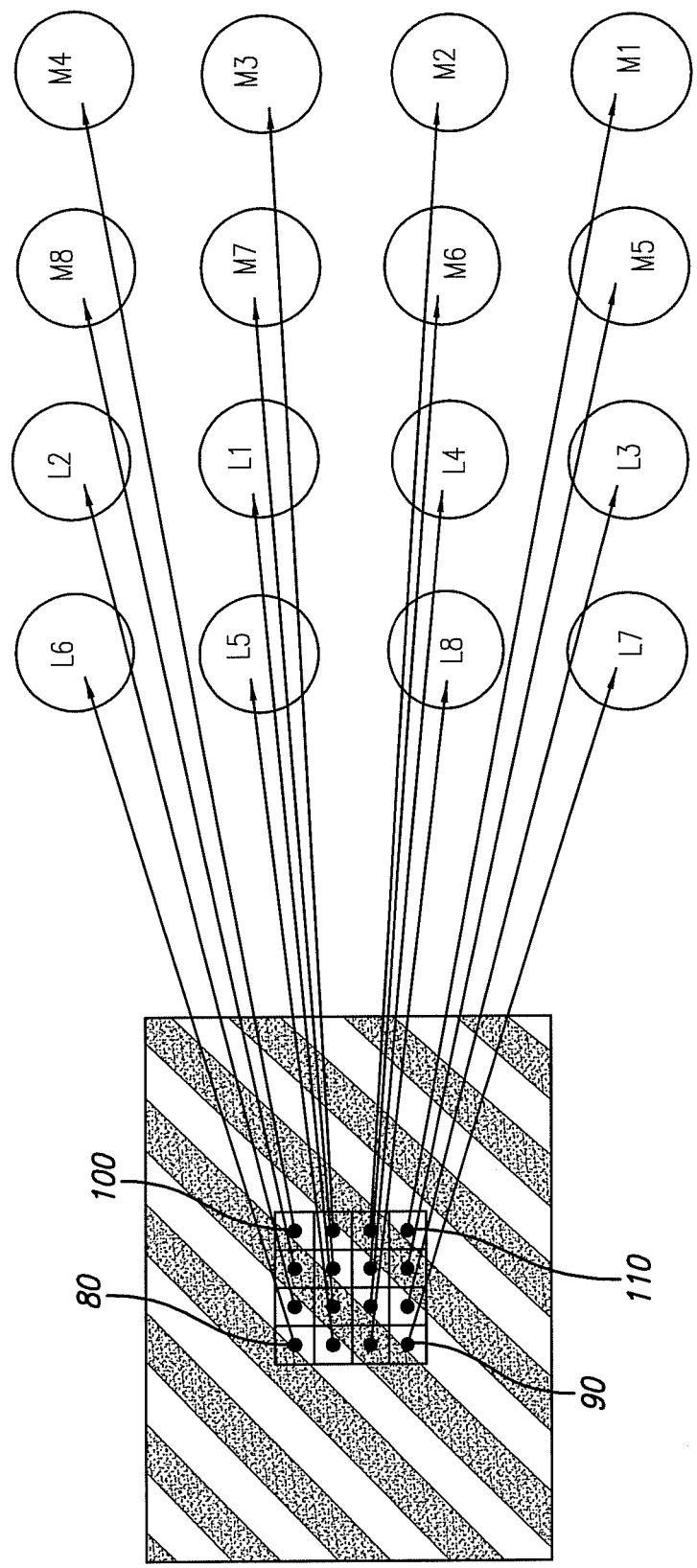
FIG. 4 is a diagram of a standard electrode mapping as known in the prior art.

As shown in the prior art embodiment of FIG. 4, usually a one-to-one spatial mapping is used. In this mapping, the locations of the individual electrodes in the retinal stimulating array are projected into the visual field. The corresponding locations of the input video image (pixels) are then mapped to the corresponding single electrode in the array. FIG. 4 shows a 4×4 prior art electrode array embodiment, where pixel (80) is mapped to electrode L6, pixel (90) is mapped to electrode L7, pixel (100) is mapped to electrode M4, pixel (110) is mapped to electrode M1, and so on, so that each pixel corresponds to a single electrode and vice versa. In other words, the corresponding locations of the input video image (pixels) are mapped to the corresponding single electrode in the array.

However, in certain cases there is a need to use a different mapping. For example, a regular spacing of stimulating electrodes may result in a distorted spatial pattern of phosphenes. Because the ganglion cell axons are stretched away from their foveal cones, a regular pattern of stimulating electrodes may result in a pattern of phosphenes that is compressed to the center of the visual field.

Figure 5:
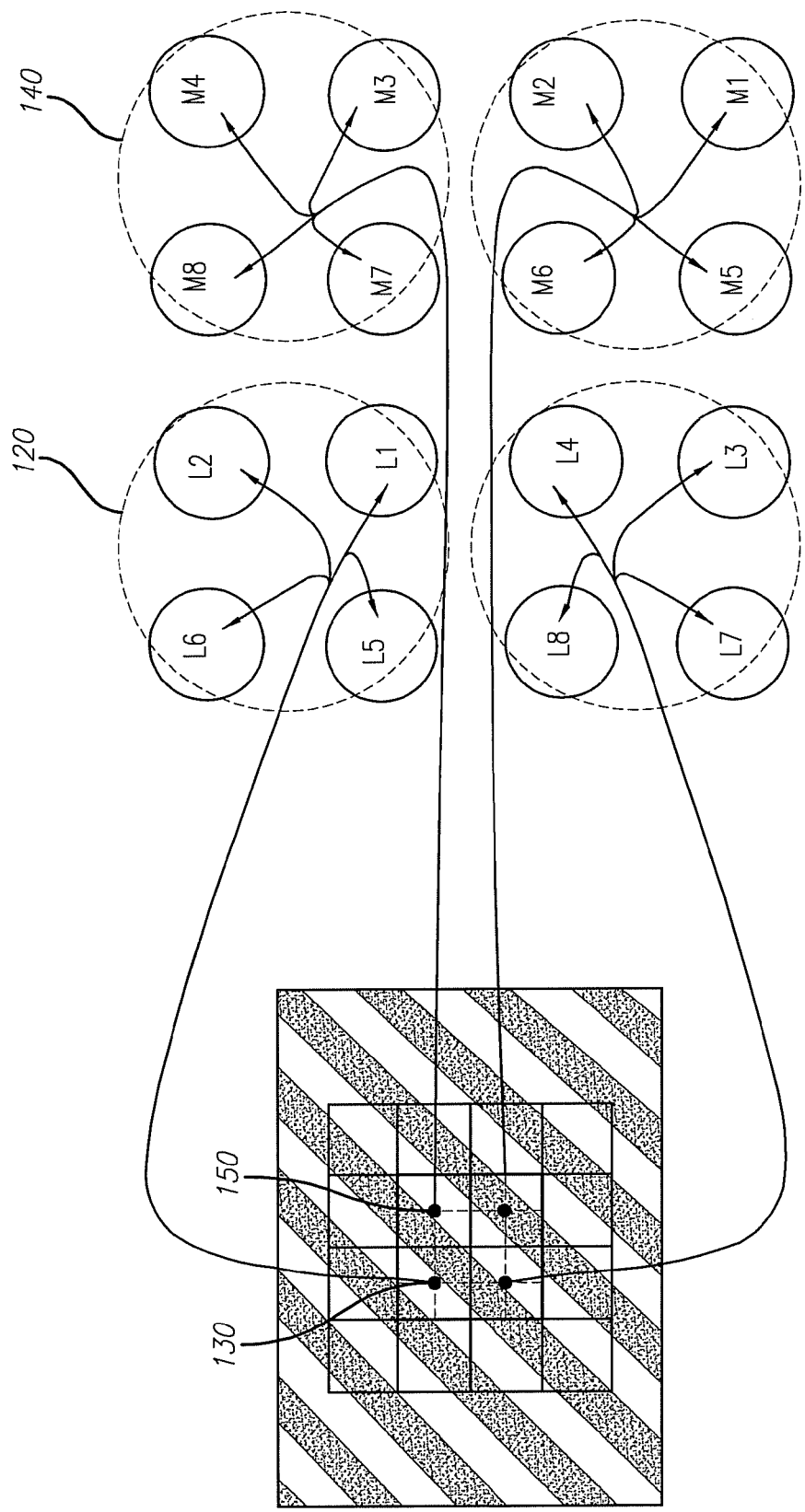
FIG. 5 is a diagram of an electrode mapping in accordance with a first embodiment of the present disclosure.

In order to address this case, applicants have altered the spatial map to undo the perceptual distortion. In particular, in cases where the patient cannot resolve the spatial information in the fine resolution of the spacing between electrodes, a group of electrodes are associated with a correspondingly large area in the video image. This is useful for cases in which areas in the array don't yield a bright percept up to the maximum allowed current. When neighboring electrodes are stimulated simultaneously, due to current summation, the percept is brighter. Grouping electrodes create "virtually" one electrode with a larger area, which enable to increase the maximum allowed current. As shown in FIG. 5, a plurality of electrodes, e.g. four electrodes, are mapped to an average of a plurality of pixels, where the number of the electrodes in the group corresponds to the number of pixels the average of which is taken. Therefore, each electrode of group (120) is mapped to a first average (130) of four pixels, each electrode of group (140) is mapped to a second average (150) of four pixels, and so on.

Figure 6:
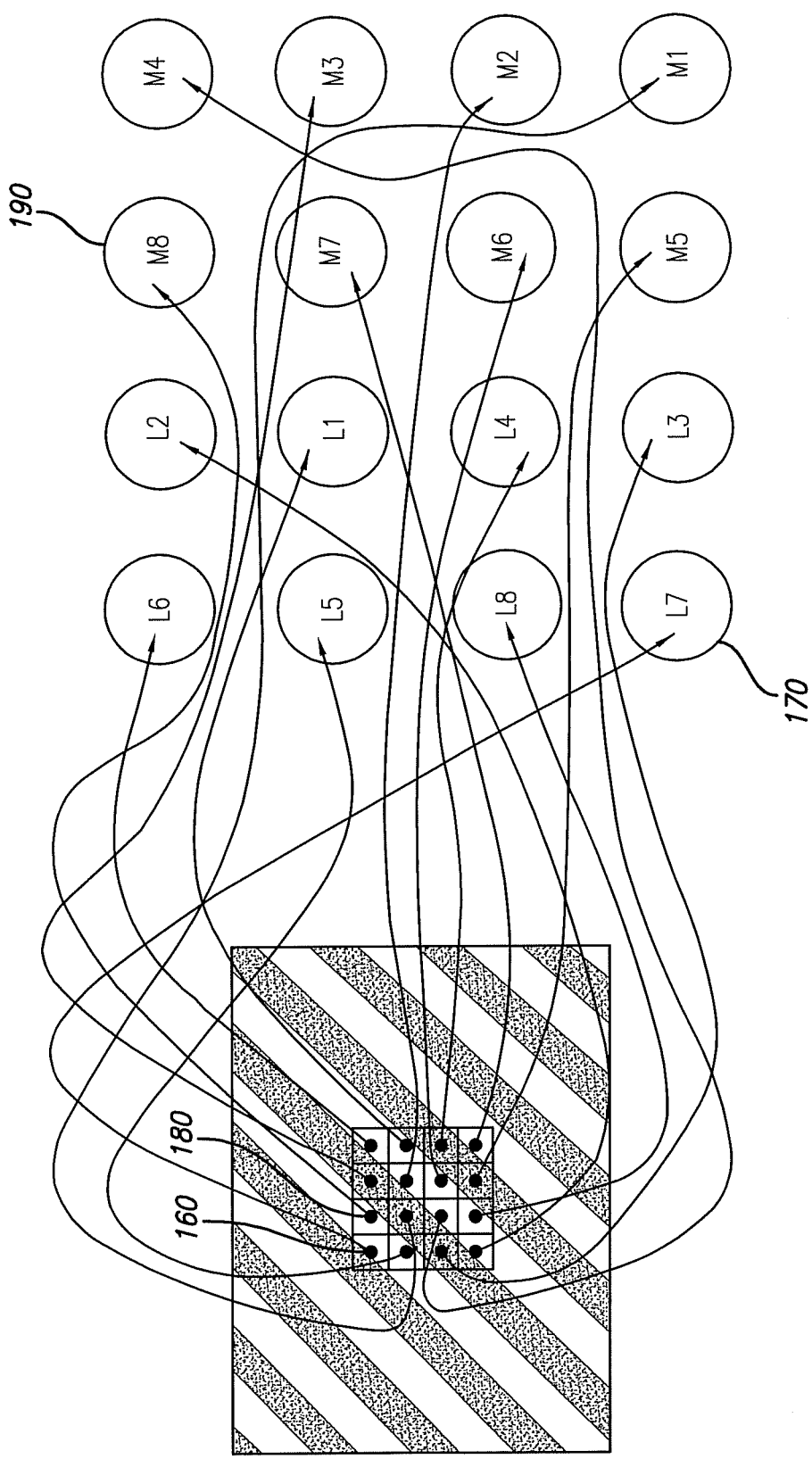
FIG. 6 is a diagram of an electrode mapping in accordance with a second embodiment of the present disclosure.

FIG. 6 shows a further embodiment of the present disclosure, where random mapping is performed. For example, pixel (160), instead of being mapped to electrode L6, is being mapped to electrode L7 (170). Similarly, pixel (180), instead of being mapped to electrode L2, is being mapped to electrode M8 (190). Random mapping can be used in order to test whether a specific subject is benefitting from spatial modulation in the array. Flexible spatial mapping can also solve wiring mistakes in the implant that are found after the implantation surgery.

A third embodiment can also be provided, which is a combination of the first two embodiments. In other words, a plurality of electrodes is randomly mapped to an average of a plurality of pixels.

The embodiments of FIGS. 5 and 6 have been shown with reference to a 4×4 electrode arrangement for the sake of simplicity. Current electrode arrangements are in a 6×10 array (e.g., electrodes A1 through F10), and the 6×10 electrode array represents the best mode of the present disclosure. The person skilled in the art will note that the embodiments of FIGS. 5 and 6 can be easily adapted to a 6×10 electrode array environment.

Therefore, in accordance with some of the embodiments of the present disclosure, an improved method of operating a visual prosthesis is disclosed. The method uses spatial maps to control neural stimulation for correcting distortions from the foveal pit, correcting wiring mistakes in the implant, bypassing broken electrodes, testing the resolution limit, testing the benefit the patient receives from correct spatial mapping, and solving orientation problems.

Accordingly, what has been shown are methods and systems for providing stimulation inputs to a visual prosthesis implant. While these methods and systems have been described by means of specific embodiments and applications thereof, it is understood that numerous modifications and variations could be made thereto by those skilled in the art without departing from the spirit and scope of the disclosure. It is therefore to be understood that within the scope of the claims, the disclosure may be practiced otherwise than as specifically described herein.

What is claimed is:

1. A method of mapping data to electrodes of a neural stimulator implant adapted to be positioned on neurons of a subject, the method comprising:
    providing a processing unit including a map for the association of data to electrodes;
    associating a plurality of geographically related input values to form a data group within the map including a plurality of input values;
    associating a plurality of electrodes to form a geographically related group of a plurality of electrodes;
    mapping the data group to the group of electrodes with a value derived from the data group being applied to the group of electrodes; and
    stimulating neural tissue with signals derived from the map.

2. The method of claim 1, wherein the group of data points exhibit an average data point value, and wherein the mapping of the group of data points to the group of electrodes results in configuring the neural stimulator implant to excite each electrode of the group of electrodes with the average data point value.

3. The method of claim 1, wherein the number of data points in the group of data points is the same as the number of electrodes in the group of electrodes.

4. The method of claim 1, wherein associating the plurality of data points and associating the plurality of electrodes are controllable associating operations.

5. The method of claim 1, wherein a total number of electrodes is 60, arranged in a 6×10 array.

6. A method of undoing perceptual distortion in a subject, comprising:
    providing the subject with a neural stimulator implant, the neural stimulator implant configured to acquire data and comprising electrodes positioned on neurons of the subject; and
    mapping the relationship of data points of the acquired data to the electrodes in accordance with the method of claim 1.

7. The method of claim 6, wherein the group of data points exhibits an average data point value, and wherein mapping of the group of data points to the group of electrodes results in configuring the neural stimulator implant to excite each electrode of the group of electrodes with the average data point value.

8. The method of claim 6, wherein the number of data points in the group of data points is the same as the number of electrodes in the group of electrodes.

9. The method of claim 6, wherein associating the plurality of data points and associating the plurality of electrodes are controllable associating operations.

* * * * *